United States Patent
Roche et al.

(10) Patent No.: US 8,337,563 B2
(45) Date of Patent: Dec. 25, 2012

(54) MOTION INDUCING REVERSE SHOULDER ASSEMBLY

(75) Inventors: Christopher P. Roche, Gainesville, FL (US); C. Michael Mauldin, Lake City, FL (US); Richard Jones, Asheville, NC (US); Thomas Wright, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 0 days.

(21) Appl. No.: 13/542,934

(22) Filed: Jul. 6, 2012

(65) Prior Publication Data
US 2012/0271426 A1    Oct. 25, 2012

Related U.S. Application Data

(62) Division of application No. 12/722,265, filed on Mar. 11, 2010, now Pat. No. 8,241,366.

(60) Provisional application No. 61/159,276, filed on Mar. 11, 2009.

(51) Int. Cl.
*A61F 2/30* (2006.01)
*A61F 2/40* (2006.01)

(52) U.S. Cl. .................. 623/19.13; 623/19.12; 623/23.4

(58) Field of Classification Search .... 623/19.11–19.14, 623/23.4, 23.42
See application file for complete search history.

(56) References Cited

U.S. PATENT DOCUMENTS

| | | | |
|---|---|---|---|
| 4,550,450 | A | 11/1985 | Kinnett |
| 7,241,314 | B1 | 7/2007 | Winslow |
| 2005/0278032 | A1 | 12/2005 | Tornier et al. |
| 2006/0079963 | A1 | 4/2006 | Hansen |
| 2007/0244563 | A1 | 10/2007 | Roche et al. |
| 2010/0234959 | A1 | 9/2010 | Roche et al. |

OTHER PUBLICATIONS

International Search Report dated May 4, 2010 form International Appln. No. PCT/US2010/027010.

*Primary Examiner* — David H Willse
*Assistant Examiner* — Javier Blanco
(74) *Attorney, Agent, or Firm* — Greenberg Traurig, LLP

(57) ABSTRACT

One embodiment of the present invention relates to a reverse shoulder assembly. Another embodiment of the present invention relates to a reverse shoulder assembly method of use. In one example, a reverse shoulder assembly of the present invention may be provided such that the reverse shoulder assembly alters the abduction force created by a patient's deltoid to a forward flexion force. In one example, a reverse shoulder assembly of the present invention may be provided such that the reverse shoulder assembly alters the abduction force created by a patient's deltoid to an external rotation force. In one example, a reverse shoulder assembly of the present invention may be provided such that the reverse shoulder assembly alters the abduction force created by a patient's deltoid to an external rotation force and a forward flexion force.

8 Claims, 8 Drawing Sheets

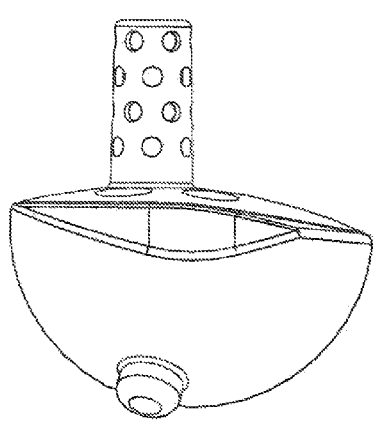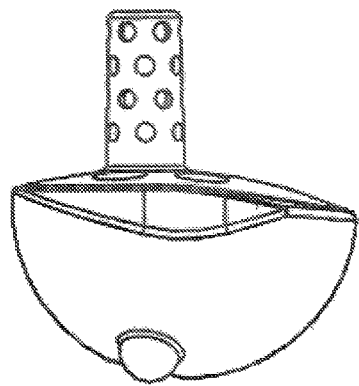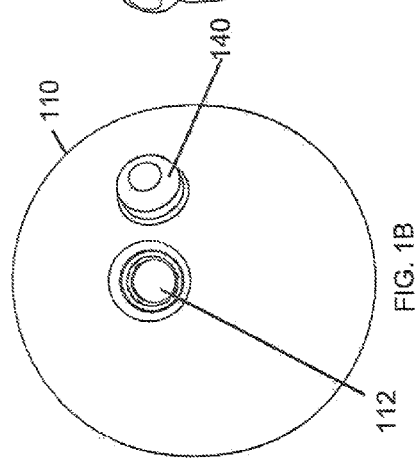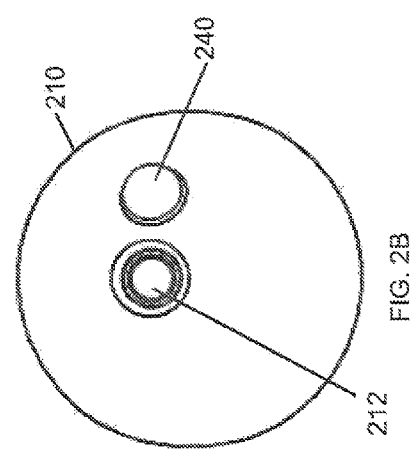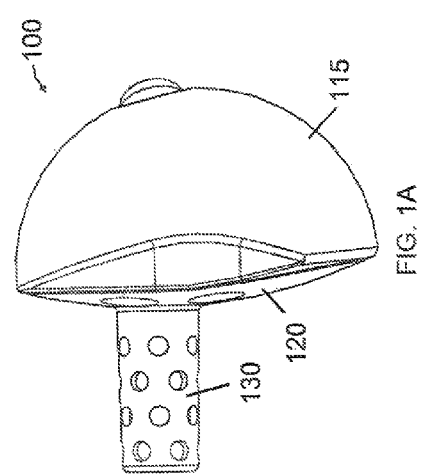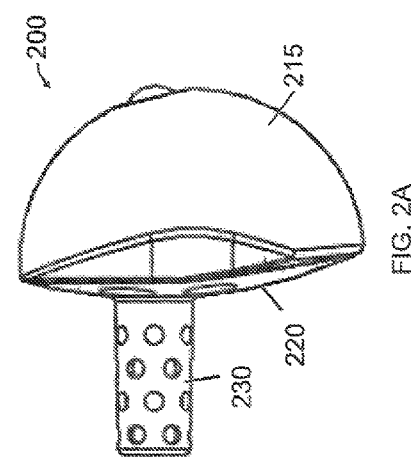

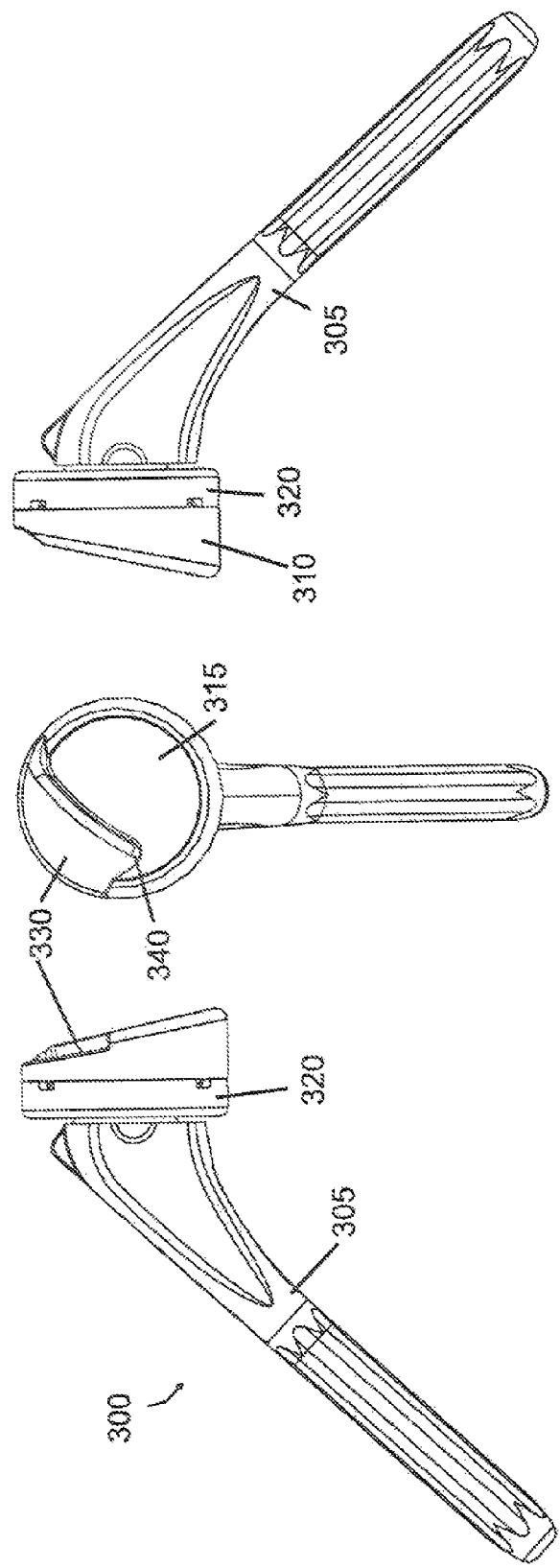

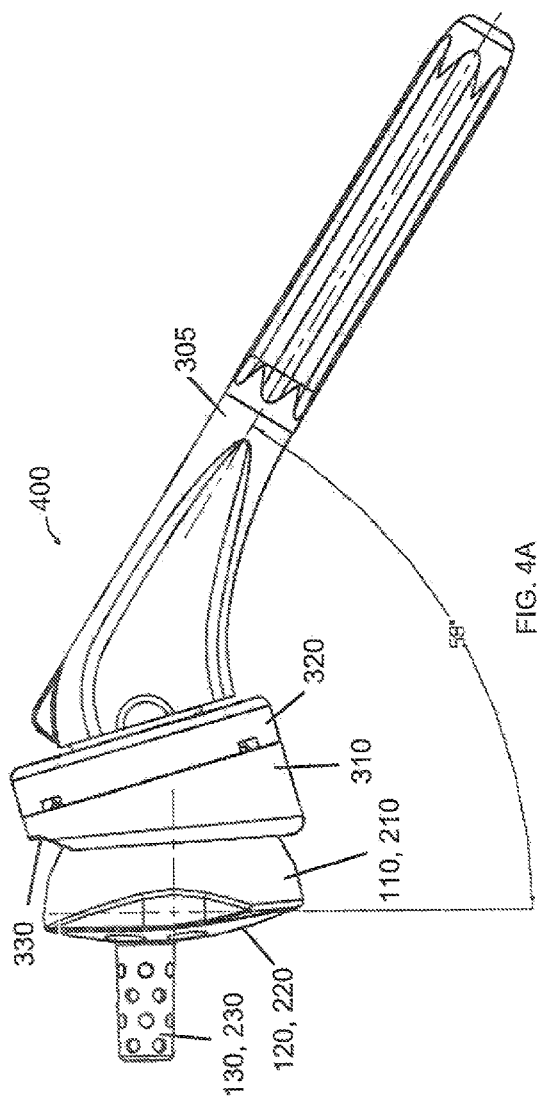
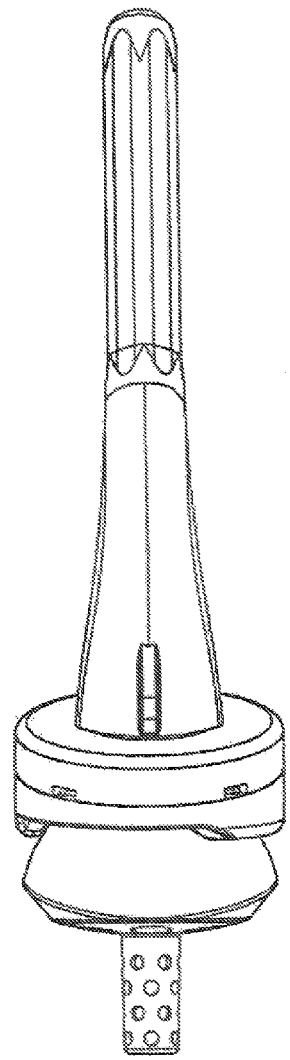

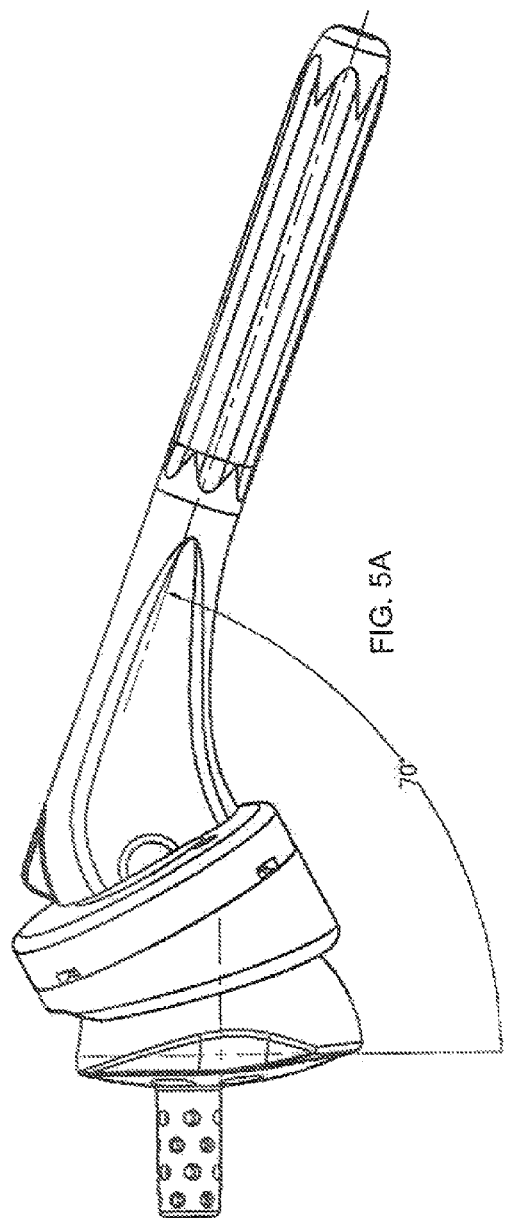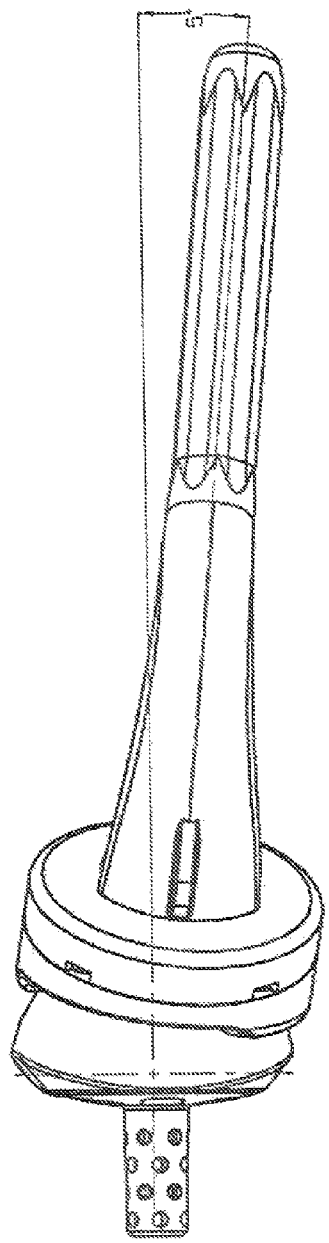
FIG. 5A
FIG. 5B

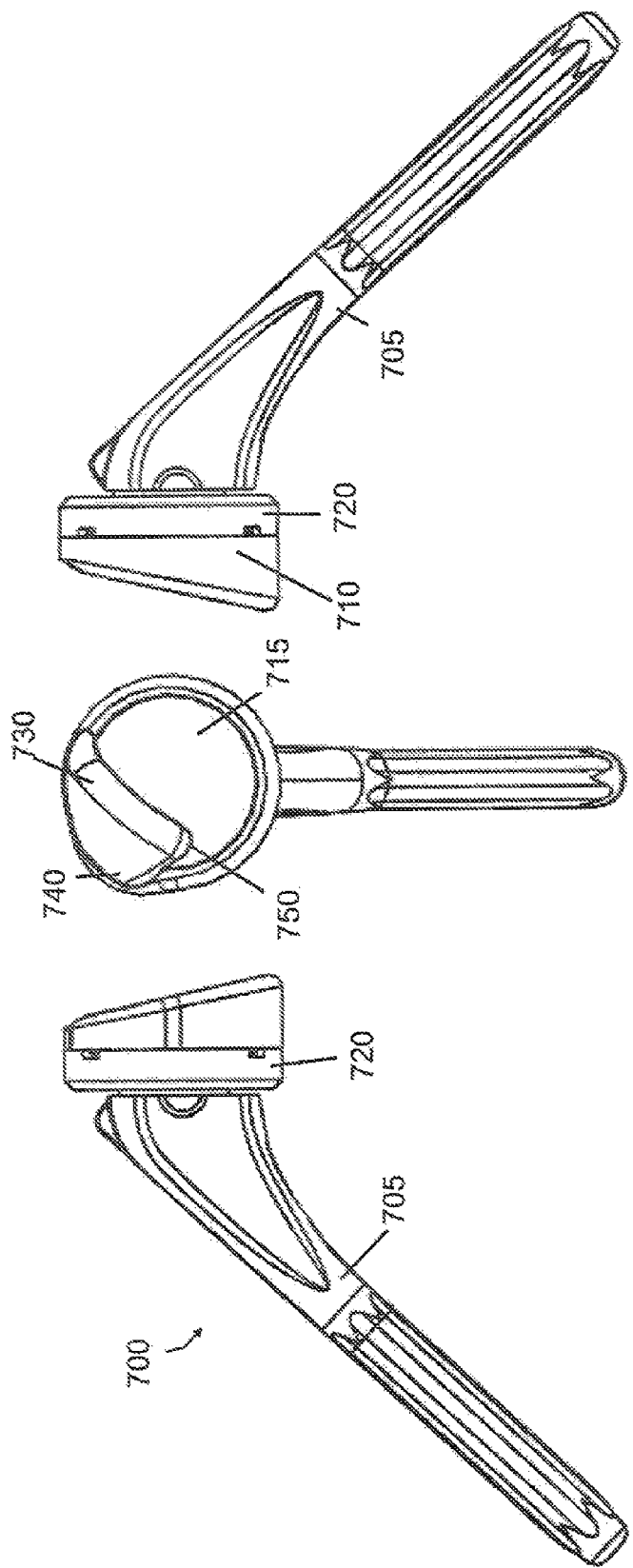

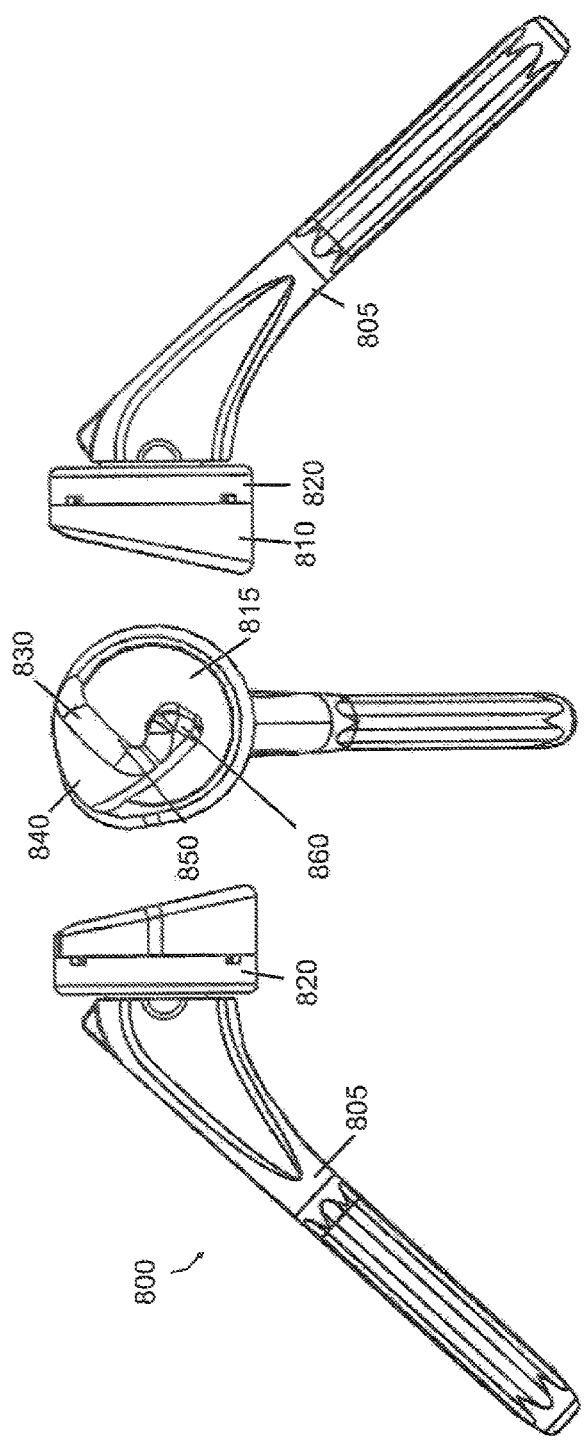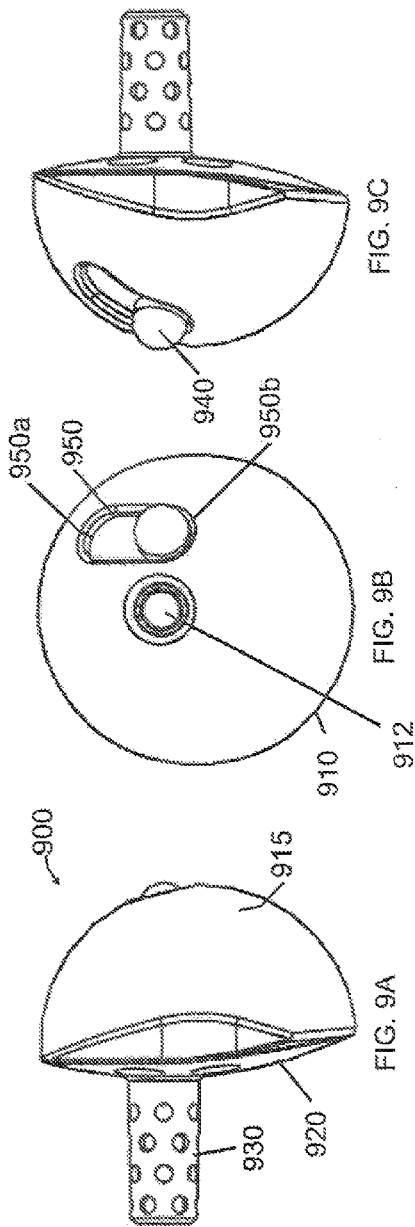

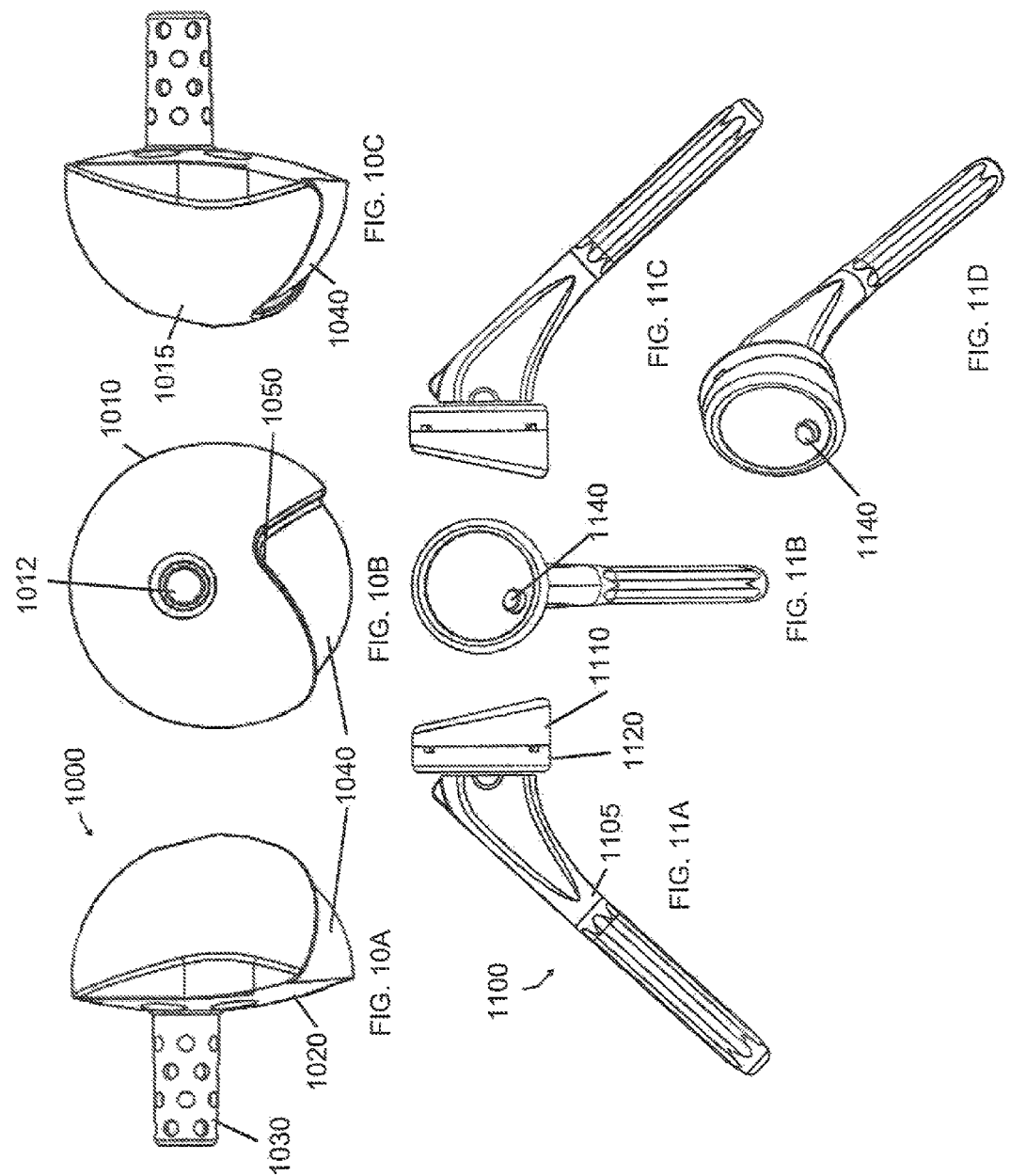

MOTION INDUCING REVERSE SHOULDER ASSEMBLY

RELATED APPLICATIONS

This application is a divisional application of U.S. patent application Ser. No. 12/722,265, filed on Mar. 11, 2010, now U.S. Pat. No. 8,241,366, which claims the benefit of and priority to U.S. Provisional Application Ser. No. 61/159,276, filed Mar. 11, 2009, the entirety of these applications are hereby incorporated herein by reference.

BACKGROUND

The reverse shoulder prosthesis has been indicated for use in patients with a nonfunctioning rotator cuff, pain, secondary arthropathy, and pseudoparalysis. Patients receiving a reverse shoulder prosthesis implantation typically have muscle deficiencies which prevent them from achieving internal or external rotation or more complex motions which require either internal or external rotation in combination with another type of motion. One such example is a clinical symptom commonly referred to as the "Hornblower's sign" or "dropping sign", a condition in which deficiencies in the external rotator muscles prevent the patient from externally rotating the arm as it is elevated and often result in the arm falling into internal rotation when the arm is elevated. External rotation is used for many activities of daily living, including, but not limited to, eating and brushing one's teeth. Some of the external rotators in the shoulder are the posterior deltoid, the infraspinatus, and the teres minor—patients with cuff tear arthropathy typically have little functional infraspinatus or teres minor.

SUMMARY

Motion inducing reverse shoulder prostheses are disclosed herein.

An embodiment of the present invention relates to a glenoid component comprising a glenosphere and a glenoid plate, wherein the glenosphere comprises an articulating surface, and wherein the articulating surface comprises a motion inducing element.

Another embodiment of the present invention relates to a humeral component comprising a humeral stem, a humeral liner, and a humeral adapter plate which connects the humeral liner to the humeral stem, wherein the humeral liner comprises a motion inducing humeral liner surface.

Another embodiment of the present invention relates to a reverse shoulder assembly comprising a motion inducing glenosphere and a motion inducing humeral liner. In an embodiment, when the reverse shoulder assembly is implanted in a patient, the reverse shoulder assembly is sufficiently designed to alter an abduction force created by the patient's deltoid to a forward flexion force. In an embodiment, when the reverse shoulder assembly is implanted in a patient, the reverse shoulder assembly is sufficiently designed to alter an abduction force created by the patient's deltoid to an external rotation force at higher levels of arm elevation. In an embodiment, when the reverse shoulder assembly is implanted in a patient, the reverse shoulder assembly is sufficiently designed to alter an abduction force created by the patient's deltoid to both a forward flexion and an external rotation force.

Another embodiment of the present invention relates to a reverse shoulder assembly comprising a glenoid component and a humeral component, wherein the glenoid component comprises an articulating surface, wherein the articulating surface comprises a motion inducing element, wherein the humeral component comprises a humeral liner, wherein the humeral liner comprises a motion inducing humeral liner surface, wherein the motion inducing element and the motion inducing humeral liner surface are sufficiently designed so that, when the glenoid component is implanted in a glenoid, and when the humeral component is implanted in a humerus, an interaction between the motion inducing element and the motion inducing humeral liner surface alters the abduction motion of the humerus relative to a scapula into a forward flexion motion of the humerus relative to the scapula. In an embodiment, the interaction between the motion inducing element and the motion inducing humeral liner surface further alters the abduction motion of the humerus relative to the scapula into an external rotation motion of the humerus relative to the scapula.

Another embodiment of the present invention relates to a glenoid component comprising a glenosphere and a glenoid plate, wherein the glenosphere comprises a motion inducing guiding surface.

Another embodiment of the present invention relates to a humeral component comprising a humeral stem, a humeral liner, and a humeral adapter plate which connects the humeral liner to the humeral stem, wherein the humeral liner comprises an articulating surface, and wherein the articulating surface comprises a motion inducing element.

Another embodiment of the present invention relates to a reverse shoulder assembly comprising a glenoid component and a humeral component, wherein the humeral component comprises a humeral liner, wherein the humeral liner comprises an articulating surface, wherein the articulating surface comprises a motion inducing element, wherein the glenoid component comprises a motion inducing guiding surface, wherein the motion inducing element and the motion inducing guiding surface are sufficiently designed so that, when the glenoid component is implanted in a glenoid, and when the humeral component is implanted in a humerus, an interaction between the motion inducing element and the motion inducing guiding surface alters the abduction motion of the humerus relative to a scapula into a forward flexion motion of the humerus relative to the scapula. In an embodiment, the interaction between the motion inducing element and the motion inducing humeral liner surface also alters the abduction motion of the humerus relative to the scapula into an external rotation motion of the humerus relative to the scapula.

Another embodiment of the present invention relates to a reverse shoulder prosthesis method of use.

Another embodiment of the present invention relates to the use of a reverse shoulder prosthesis in patients with either internal or external rotation deficiencies—where the placement of a guiding feature on the glenosphere and/or on the mating humeral liner supplements these rotary deficiencies via the articulation of geometric surfaces and/or guiding features which prevent and/or constrain the prosthesis from falling in a direction opposing the deficiency (e.g., constraints to prevent prosthesis from falling into internal rotation due to the absence of the external rotation force couple caused by a external rotator deficiency).

Another embodiment of the present invention relates to a reverse shoulder assembly provide for surface(s) which maintain multiple positions of stability (e.g., where one position of stability is used for one group of motions and another position of stability is used for another group of motions).

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 1A-1C show an embodiment of a glenoid component of the present invention.

FIGS. 2A-2C show an embodiment of a glenoid component of the present invention.

FIGS. 3A-3C show an embodiment of a humeral component of the present invention.

FIGS. 4A and 4B show an embodiment of the interaction between various components of a reverse shoulder assembly of the present invention at approximately 60 degree arm abduction.

FIGS. 5A and 5B show an embodiment of the interaction between various components of a reverse shoulder assembly of the present invention at approximately 70 degree arm abduction.

FIGS. 7A-7C show an embodiment of a humeral component of the present invention.

FIGS. 8A-8C show an embodiment of a humeral component of the present invention.

FIGS. 9A-9C show an embodiment of a glenoid component of the present invention.

FIGS. 10A-10C show an embodiment of a glenoid component of the present invention.

FIGS. 11A-11D show an embodiment of a humeral component of the present invention.

Figure 6A:
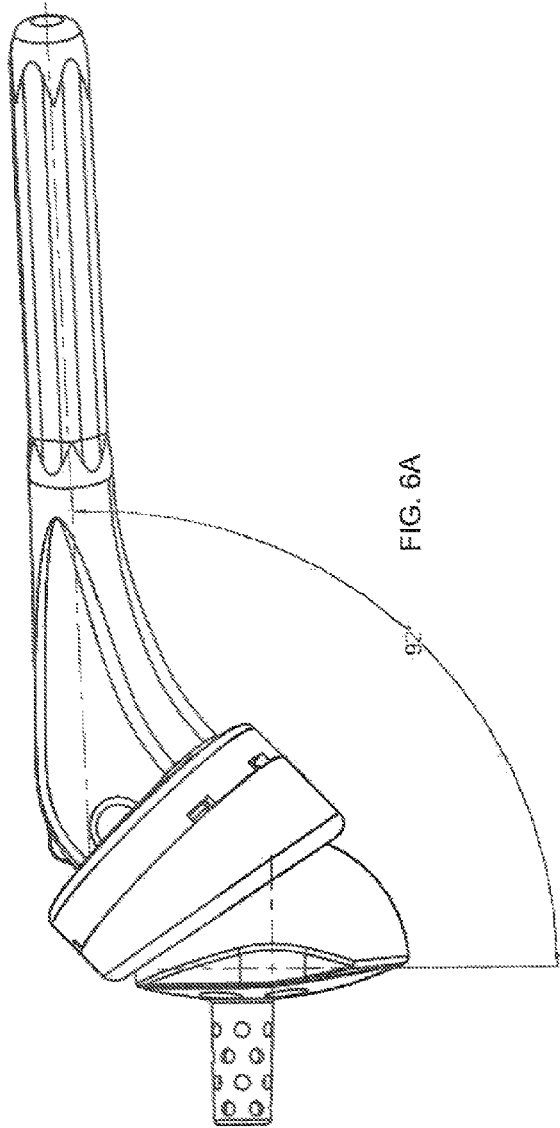
FIGS. 6A and 6B show an embodiment of the interaction between various components of a reverse shoulder assembly of the present invention at approximately 90 degree or full abduction.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components (and any size, material and similar details shown in the figures are, of course, intended to be illustrative and not restrictive). Therefore, specific structural and functional details disclosed herein are not to be interpreted as limiting, but merely as a representative basis for teaching one skilled in the art to variously employ the present invention.

As described herein, various embodiments of the present invention provide a motion inducing element (e.g., on a glenosphere and/or a humeral liner) that induces forward flexion at higher levels of arm abduction (while providing little or no limiting or constraining motion at lower levels of abduction). Further, as described herein, various embodiments of the present invention provides a reverse shoulder assembly that enable one type of motion to be altered to another type of motion.

As used herein, the terms "reverse shoulder prosthesis", "reverse shoulder assembly", "reverse shoulder system", "reverse total shoulder prosthesis" and "reverse shoulder implant" may be used interchangeably throughout the description.

FIGS. 1A-1C show an embodiment of a glenoid component 100 of the present invention. Glenoid component 100 comprises a convex glenosphere 110 and a glenoid plate 120. In an embodiment, the glenosphere 110 and the glenoid plate 120 may be formed as in integral unit. In an embodiment, the glenosphere 110 and the glenoid plate 120 are two distinct components affixed together in a modular configuration. In an embodiment, the glenosphere 110 is assembled to the glenoid plate 120 using an assembly bolt passing through hole 112. In an embodiment, the glenosphere 110 does not include hole 112. Glenosphere 110, which may be constructed, for example, from cobalt chrome, includes a convex articulating surface 115 having a motion inducing cylindrical element 140. In an embodiment, the motion inducing cylindrical element 140 has a diameter ranging from about 0.08 inches to about 0.50 inches, from about 0.10 inches to about 0.40 inches, from about 0.20 inches to about 0.30 inches. In an embodiment, the motion inducing cylindrical element 140 has a diameter of about 0.25 inches. In an embodiment, the motion inducing cylindrical element 140 has a height ranging from about 0.035 inches to about 0.250 inches, from about 0.040 inches to about 0.155 inches, from about 0.045 inches to about 0.150 inches, from about 0.050 inches to about 0.145 inches, from about 0.055 inches to about 0.140 inches, from about 0.060 inches to about 0.135 inches, from about 0.065 inches to about 0.130 inches, from about 0.070 inches to about 0.125 inches, from about 0.075 inches to about 0.120 inches, from about 0.080 inches to about 0.115 inches. In an embodiment, the motion inducing cylindrical element 140 has a height of about 0.14 inches. In an embodiment, the glenoid plate 120, which may be constructed, for example, from titanium, includes a bone "through-growth" cage stem 130 which enables bone graft to be injected (e.g., via syringe) through the front of the plate and/or placed through the hole in the bottom surface of the cage stem 130. In an embodiment, the bone "through-growth" cage stem 130 is superiorly shifted (for example, by about 4 mm) from the central point of the vertical dimension on the glenoid plate 120—enabling a surgeon to maintain the traditional surgical technique with the reverse as would be performed for total shoulder arthroplasty (i.e., drilling a hole in the center of the glenoid where the defect would occur; thereby conserving bone). In an embodiment, the motion inducing cylindrical element 140 is superiorly shifted (for example, by about 4 mm) from the central point of the vertical dimension on the articulating surface 115 of the glenosphere 110. In an embodiment, the glenoid plate 120 has the following dimensions/features: 29 mm diameter, 5 mm taper, 20 mm length bone "through-growth" cage stem 130 with screw holes having a spherical base allowing compression screws to be angled at about 15°, each hole having a threaded portion for attachment of a locking cap screw.

In an embodiment, the glenosphere 110 and the glenoid plate 120 are components of a reverse shoulder assembly of the present invention which may be implanted at a shoulder joint of a patient. During use, the motion inducing cylindrical element 140 is sufficiently designed and positioned on the articulating surface 115 so as to alter the direction of induced motion at varying humeral positions. By selecting the positioning of the motion inducing cylindrical element 140 on the articulating surface 115, different types of motion can be induced. In an embodiment, the motion inducing cylindrical element 140 is positioned on the articulating surface 115 so that when the patient raises his/her arm out to the side (i.e., shoulder abduction or lateral arm raise), the abduction motion is altered into an external rotation motion. In an embodiment, the motion inducing cylindrical element 140 is positioned on the articulating surface 115 so that when the patient raises his/her arm out to the side (i.e., shoulder abduction or lateral arm raise), the abduction motion is altered into a forward flexion motion. In an embodiment, the motion inducing cylindrical element 140 is positioned on the articulating surface 115 so that when the patient raised his/her arm out to the side (i.e., shoulder abduction or lateral arm raise), the abduction motion is altered into an external rotation and a forward flexion motion.

FIGS. 2A-2C show an embodiment of a glenoid component 200 of the present invention. Glenoid component 200 comprises a glenosphere 210 and a glenoid plate 220. In an embodiment, the glenosphere 210 and the glenoid plate 220 are two distinct components affixed together in a modular configuration. In an embodiment, the glenosphere 210 is assembled to the glenoid plate 220 using an assembly bolt passing through hole 212. In an embodiment, the glenosphere 210 does not include hole 212. In an embodiment, the glenosphere 210 and the glenoid plate 220 may be formed as in integral unit. Glenosphere 210, which may be constructed, for example, from cobalt chrome, comprises a convex articulating surface 215 having a motion inducing spherical element 240. In an embodiment, the motion inducing spherical element 240 has a diameter ranging from about 0.08 inches to about 0.50 inches, from about 0.10 inches to about 0.40 inches, from about 0.20 inches to about 0.30 inches. In an embodiment, the motion inducing spherical element 240 has a diameter of about 0.25 inches. In an embodiment, the motion inducing spherical element 240 has a height ranging from about 0.035 inches to about 0.250 inches, from about 0.040 inches to about 0.155 inches, from about 0.045 inches to about 0.150 inches, from about 0.050 inches to about 0.145 inches, from about 0.055 inches to about 0.140 inches, from about 0.060 inches to about 0.135 inches, from about 0.065 inches to about 0.130 inches, from about 0.070 inches to about 0.125 inches, from about 0.075 inches to about 0.120 inches, from about 0.080 inches to about 0.115 inches. In an embodiment, the motion inducing spherical element 240 has a height of about 0.14 inches. In an embodiment, the glenoid plate 220, which may be constructed, for example, from titanium, includes a bone "through-growth" cage stem 230 which enables bone graft to be injected (e.g., via syringe) through the front of the plate and/or placed through the hole in the bottom surface of the cage stem 230. In an embodiment, the bone "through-growth" cage stem 230 is superiorly shifted (for example, by about 4 mm) from the central point of the vertical dimension on the glenoid plate 220—enabling a surgeon to maintain the traditional surgical technique with the reverse as would be performed for total shoulder arthroplasty (i.e., drilling a hole in the center of the glenoid where the defect would occur; thereby conserving bone). In an embodiment, the motion inducing cylindrical element 240 is superiorly shifted (for example, by about 4 mm) on the articulating surface 215 of the glenosphere 210. In an embodiment, the glenoid plate 220 has the following dimensions/features: 29 mm diameter, 5 mm taper, 20 mm length bone "through-growth" cage stem 230 with screw holes having a spherical base allowing compression screws to be angled at about 15°, each hole having a threaded portion for attachment of a locking cap screw.

In an embodiment, the glenosphere 210 and the glenoid plate 220 are components of a reverse shoulder assembly of the present invention which may be implanted at a shoulder joint in a patient. During use, the motion inducing spherical element 240 is sufficiently designed and positioned on the articulating surface 215 so as to alter the direction of induced motion at varying humeral positions. By selecting the positioning of the motion inducing spherical element 240 on the articulating surface 215, different types of motion can be induced. In an embodiment, the motion inducing spherical element 240 is positioned on the articulating surface 215 so that when the patient raises his/her arm out to the side (i.e., shoulder abduction or lateral arm raise), the abduction motion is altered into an external rotation motion. In an embodiment, the motion inducing spherical element 240 is positioned on the articulating surface 215 so that when the patient raises his/her arm out to the side (i.e., shoulder abduction or lateral arm raise), the abduction motion is altered into a forward flexion motion. In an embodiment, the motion inducing spherical element 240 is positioned on the articulating surface 215 so that when the patient raises his/her arm out to the side (i.e., shoulder abduction or lateral arm raise), the abduction motion is altered into an external rotation and a forward flexion motion.

FIGS. 3A-3C show an embodiment of a humeral component 300 of the present invention. Humeral component 300 comprises a humeral stem 305, which may be used in either pressfit or cemented applications and may be constructed, for example from titanium; a humeral liner 310, which may be constructed, for example, from UHMWPE; and a humeral adapter plate 320, which connects the humeral liner 310 to the humeral stem 305 and may be constructed, for example, from titanium. Humeral liner 310 comprises a concave articulating surface 315 that is sufficiently designed to engage with the convex articulating surface 115 or 215 of the glenosphere 110 or 210; a recess area 330; and a motion inducing humeral liner surface 340 that is sufficiently designed to engage with the motion inducing element 140 or 240 of the glenosphere 110 or 210. In an embodiment, the motion inducing humeral liner surface 340 engages the motion inducing element 140 or 240 and provides a surface for the motion inducing element 140 or 240 to move or travel along, back and forth. In an embodiment, the humeral liner 310 may be provided in varying thicknesses (for example, +0, +2.5 mm). In an embodiment, the recess area 330 has a depth that is variable and is from about 0.040 inches to about 0.255 inches, from about 0.035 inches to about 0.250 inches, from about 0.040 inches to about 0.155 inches, from about 0.045 inches to about 0.150 inches, from about 0.050 inches to about 0.145 inches, from about 0.055 inches to about 0.140 inches, from about 0.060 inches to about 0.135 inches, from about 0.065 inches to about 0.130 inches, from about 0.070 inches to about 0.125 inches, from about 0.075 inches to about 0.120 inches, from about 0.080 inches to about 0.115 inches. In an embodiment, the recess area 330 has a depth of about 0.19 inches. In an embodiment, the depth of the recess area 330 is measured from the articulating surface 315.

In an embodiment, the humeral component 300 and the glenoid component 100 or 200 form a reverse shoulder assembly of the present invention which may be implanted at a shoulder joint in a patient. In an embodiment, the amount of material recessed from the articulating surface 315 is variable and is dependent upon the specific angle of abduction in which it is desired that the motion inducing features become engaged. In an embodiment, the depth of the recess area 330 is determined after selecting the height of the motion inducing element 140 or 240. In an embodiment, the depth of the recess area 330 is larger than the height of the motion inducing element 140 or 240 so that when the motion inducing element 140 or 240 interacts with the motion inducing humeral liner surface 340, the convex articulating surface 115 or 215 does not contact the recess area 330.

FIGS. 4A, 4B, 5A, 5B, 6A and 6B show embodiments of the interaction between various components of a reverse shoulder assembly 400 of the present invention at various degrees of shoulder abduction. The reverse should assembly 400 includes the humeral component 300 of FIGS. 3A-3C (humeral stem 305, humeral liner 310, and humeral adapter plate 320) and the glenoid component 100 or 200 of FIGS. 1A-1C and FIGS. 2A-2C, respectively (glenosphere 110 or 210 and glenoid plate 120 or 220). Of note, the shoulder joint (e.g., the clavicle, the scapula, the humerus, and the associated muscles, ligaments, and tendons) is not illustrated in FIGS. 4A, 4B, 5A, 5B, 6A and 6B. Although not illustrated, in some embodiments screws and fixation devices may be used for assembly of the individual components to one another and for assembly of the construct to the native bone (these elements may be constructed, for example, from titanium).

In an embodiment, the reverse shoulder assembly 400 may be used to treat patients having a condition including, but not limited to, rotator cuff tear arthroplasty, instability with anterosuperior escape, pseudoparalysis, and failures of surgery for arthritis and facture management In an embodiment, the reverse shoulder assembly 400 may be used for patients with rotator cuff tear arthropathy (end stage cuff tear arthropathy) a medical condition in which the rotator cuff muscles (the muscles around the shoulder joint) have degenerated, or weakened to a point where they can no longer hold the shoulder joint intact or allow it to function normally in conjunction with arthritis. In an embodiment, the reverse shoulder assembly 400 may be used for patients needing revision surgery, for failed shoulder replacement and shoulder fractures. In an embodiment, the reverse shoulder assembly 400 may be used for patients who do not have a rotator cuff (pseudo-paralytic shoulder).

It should be understood that the glenoid plate 120 or 220 would be implanted in the glenoid of the patient, and the humeral stem 305 would be implanted into the humerus of the patient. In an embodiment, the bone "through-growth" cage stem 130 or 230 is superiorly shifted (for example, by about 4 mm) from the central point of the vertical dimension on the glenoid plate 120 or 220 so that when the glenoid plate 120 or 220 is implanted in a glenoid bone, the bone "through-growth" cage stem 130 or 230 is positioned in a center of the glenoid bone, and a distal rim of the glenoid plate 120 or 220 is aligned with a distal edge of an articular surface of the glenoid bone. In an embodiment, the motion inducing element 140 or 240 of the glenosphere 110 or 210 and the motion inducing humeral liner surface 340 of the humeral liner 310 are sufficiently designed so that, when implanted, an interaction between the motion inducing element 140 or 240 and the motion inducing humeral liner surface 340 alters the abduction motion of a humerus relative to a scapula into a forward flexion motion of the humerus relative to the scapula. In an embodiment, the motion inducing element 140 or 240 of the glenosphere 110 or 210 and the motion inducing humeral liner surface 340 of the humeral liner 310 are sufficiently designed so that, when implanted, an interaction and movement between the motion inducing element 140 or 240 and the motion inducing humeral liner surface 340 alters the abduction motion of a humerus relative to a scapula into an external rotation motion of the humerus relative to the scapula. In an embodiment, the motion inducing element 140 or 240 of the glenosphere 110 or 210 and the motion inducing humeral liner surface 340 of the humeral liner 310 are sufficiently designed so that, when implanted, an interaction between the motion inducing element 140 or 240 and the motion inducing humeral liner surface 340 alters the abduction motion of a humerus relative to a scapula into an external rotation and a forward flexion motion of the humerus relative to the scapula.

Figure 6B:
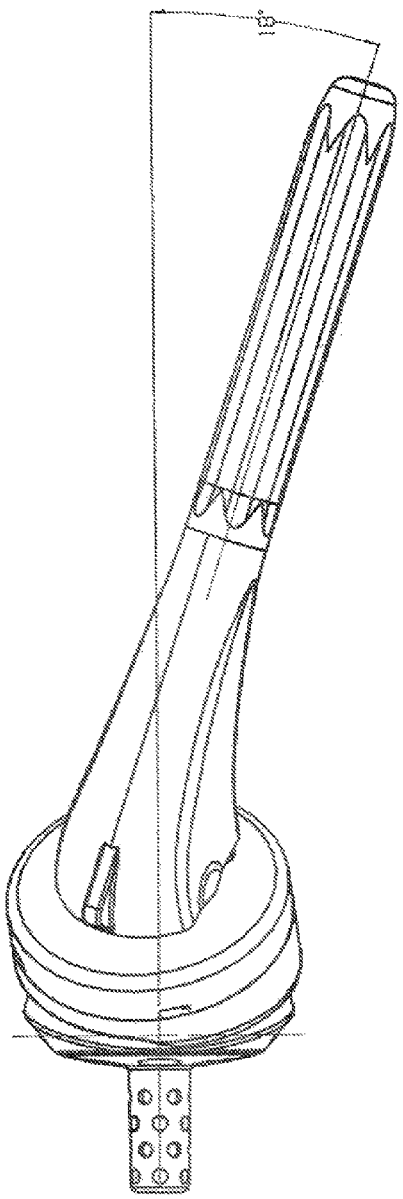

In an embodiment, the motion inducing element 140 or 240 of the glenosphere 110 or 210 is sized and positioned on the glenosphere 110 or 210 so that the motion inducing element does not inhibit internal and/or external rotation at lower levels of arm elevation. The point at which the motion inducing element 140 or 240 of the glenosphere 110 or 210 contacts the motion inducing humeral liner surface 340 of the humeral liner 310 can change depending upon the glenosphere 110 or 210 and humeral liner 310 geometry (specifically, the location of the motion inducing element 140 or 240 and the amount of material recessed from the humeral liner 310). In an embodiment, the point occurs between about 130 degrees and about 90 degrees shoulder abduction. As illustrated in FIGS. 4A and 4B, the motion inducing element 140 or 240, and the motion inducing humeral liner surface 340 are sufficiently designed so that, when the glenoid plate 120 or 220 is implanted in the glenoid of the patient, the humeral stem 305 is implanted in the humerus of the patient, and the patient raises his/her arm to approximately 60 degree shoulder abduction, the motion inducing humeral liner surface 340 engages the motion inducing element 140 or 240. As illustrated in FIGS. 5A and 5B, as the patient raises his/her arm from approximately 60 degree shoulder abduction to approximately 70 degree shoulder abduction, the motion inducing element 140 or 240 moves along the motion inducing humeral liner surface 340 and induces forward flexion of the humerus (i.e., approximately 10 degrees of forward flexion). In the embodiment illustrated in FIGS. 5A and 5B, the abduction motion also induces an external rotation motion. As illustrated in FIGS. 6A and 6B, as the patient raises his/her arm to approximately 90 degree shoulder abduction (i.e., full abduction) the motion inducing element 140 or 240 continues to move along the motion inducing humeral liner surface 340, further inducing forward flexion of the humerus (i.e., for a total of approximately 20 degrees of forward flexion). In the embodiment illustrated in FIGS. 6A and 6B, the abduction motion also induces an external rotation motion.

FIGS. 7A-7C show an embodiment of a humeral component 700 of the present invention. Humeral component 700 comprises a humeral stem 705, which may be used in either pressfit or cemented applications and may be constructed, for example from titanium; a humeral liner 710, which may be constructed, for example, from UHMWPE; and a humeral adapter plate 720, which connects the humeral liner 710 to the humeral stem 705 and may be constructed, for example, from titanium. Humeral liner 710 comprises a concave articulating surface 715 that is sufficiently designed to engage with a convex articulating surface of a glenosphere of the present invention; a motion inducing humeral liner surface 750; and a recess area 730 having a posterior hood 740, the posterior hood 740 sufficiently designed to increase stability of a reverse shoulder assembly during use. The motion inducing humeral liner surface 750 is sufficiently designed to engage with a motion inducing element of a glenosphere of the present invention. In an embodiment, the motion inducing humeral liner surface 750 engages the motion inducing element and provides a surface for the motion inducing element to move or travel along, back and forth. In an embodiment, the humeral liner 710 may be provided in varying thicknesses (e.g., +0, +2.5 mm). In an embodiment, the recess area 730 has a depth that is variable and is from about 0.040 inches to about 0.255 inches, from about 0.035 inches to about 0.250 inches, from about 0.040 inches to about 0.155 inches, from about 0.045 inches to about 0.150 inches, from about 0.050 inches to about 0.145 inches, from about 0.055 inches to about 0.140 inches, from about 0.060 inches to about 0.135 inches, from about 0.065 inches to about 0.130 inches, from about 0.070 inches to about 0.125 inches, from about 0.075 inches to about 0.120 inches, from about 0.080 inches to about 0.115 inches. In an embodiment, the recess area 730 has a depth of about 0.19 inches. In an embodiment, the depth of the recess area 730 is measured from the articulating surface 715.

In an embodiment, the humeral component 700 and a glenoid component of the present invention form a reverse shoulder assembly of the present invention which may be implanted at a shoulder joint in a patient. In an embodiment, the amount of material recessed from the articulating surface 715 is variable and is dependent upon the specific angle of abduction in which it is desired that the motion inducing features become engaged. In an embodiment, the depth of the recess area 730 is determined after selecting the height of a motion inducing element of a glenosphere of the present invention. The depth of the recess area 730 should be larger than the height of the motion inducing element of the glenosphere so that when the motion inducing element interacts with the motion inducing humeral liner surface 750, the convex articulating surface of the glenosphere does not contact the recess area 730.

In an embodiment, the humeral component 700 and a glenoid component of the present invention form a reverse shoulder assembly used for treating rotator cuff tear arthroplasty. In such embodiments, the posterior hood 740 of the recess area 730 is sufficiently designed to prevent the motion inducing element from falling away from the direction of the muscle deficiency. In an embodiment, the posterior hood 740 comprises a raised geometry (e.g., on the anterior/superior side for a posterior deficient glenoid; on the posterior/superior side for an anterior deficient glenoid) to prevent the motion inducing element from falling into internal rotation due to the absence of the external rotation force couple caused by an external rotator deficiency.

FIGS. 8A-8C show an embodiment of a humeral component 800 of the present invention. Humeral component 800 comprises a humeral stem 805, which may be used in either pressfit or cemented applications and may be constructed, for example from titanium; a humeral liner 810, which may be constructed, for example, from UHMWPE; and a humeral adapter plate 820, which connects the humeral liner 810 to the humeral stem 805 and may be constructed, for example, from titanium. Humeral liner 810 comprises a concave articulating surface 815 that is sufficiently designed to engage with a convex articulating surface of a glenosphere of the present invention; a motion inducing humeral liner surface 850 that is sufficiently designed to engage with a motion inducing element of a glenosphere of the present invention; and a recess area 830 having a posterior hood 840, the posterior hood 840 sufficiently designed to provide extra surface area to prevent the motion inducing element from impinging on anything (bone, implant, tissue, etc) which could potentially cause dislocation (via lever-out). In an embodiment, the motion inducing humeral liner surface 850 engages the motion inducing element and provides a surface for the motion inducing element to move or travel along, back and forth. In an embodiment, the humeral liner 810 may be provided in varying thicknesses (e.g., +0, +2.5 mm). At least one end of the motion inducing humeral liner surface 850 terminates in a groove 860 that is sufficiently designed to create a position of stability via mechanical interlock with the motion inducing element of the glenosphere. In an embodiment, the groove 860 is a track which the motion inducing element can follow to a second position of stability; this second position of stability locks the motion inducing element in a specific location and may allow a patient to perform additional motion in that specific orientation. In an embodiment, this position of stability aids a patient in maintaining his/her arm in a given position (thereby balancing the internal rotation force with a mechanical interlock—as the external rotation force may be essentially nonexistent via the deficient muscle).

In an embodiment, the recess area 830 has a depth that is variable and is from about 0.040 inches to about 0.255 inches, from about 0.035 inches to about 0.250 inches, from about 0.040 inches to about 0.155 inches, from about 0.045 inches to about 0.150 inches, from about 0.050 inches to about 0.145 inches, from about 0.055 inches to about 0.140 inches, from about 0.060 inches to about 0.135 inches, from about 0.065 inches to about 0.130 inches, from about 0.070 inches to about 0.125 inches, from about 0.075 inches to about 0.120 inches, from about 0.080 inches to about 0.115 inches. In an embodiment, the recess area 830 has a depth of about 0.19 inches. In an embodiment, the depth of the recess area 830 is measured from the articulating surface 815.

In an embodiment, the humeral component 800 and a glenoid component of the present invention form a reverse shoulder assembly. In an embodiment, the amount of material recessed from the articulating surface 815 is variable and is dependent upon the specific angle of abduction in which it is desired that the motion inducing features become engaged. In an embodiment, the depth of the recess area 830 is determined after selecting the height of the motion inducing element. In an embodiment, the depth of the recess area 830 should be larger than the height of the motion inducing element so that when the motion inducing element interacts with the motion inducing humeral liner surface 850, the convex articulating surface of the glenosphere does not contact the recess area 830.

In an embodiment, the humeral component 800 and a glenoid component of the present invention form a reverse shoulder assembly. In an embodiment, the humeral component 800 and the glenoid component form a reverse shoulder assembly of the present invention used for treating rotator cuff tear arthroplasty. In such embodiments, the posterior hood 840 of the recess area 830 is sufficiently designed to prevent the assembly from falling away from the direction of the muscle deficiency. The posterior hood 840 may comprise a raised geometry (e.g., on the anterior/superior side for a posterior deficient glenoid; on the posterior/superior side for an anterior deficient glenoid) to prevent the motion inducing element from falling into internal rotation due to the absence of the external rotation force couple caused by an external rotator deficiency.

In some embodiments of the present invention, the motion inducing element of the glenosphere is sufficiently designed to remain stationary on the convex articulating surface of the glenosphere during interaction between the motion inducing element and a motion inducing humeral liner surface. However, it may be desirable to have a motion inducing element on a glenosphere that is modular, i.e., does not remain stationary on the convex articulating surface of the glenosphere during interaction between the motion inducing element and a motion inducing humeral liner surface. In such embodiments, the motion inducing element is sufficiently designed to move within a slot of selectable length having a first end and a second end, wherein during abduction motion the motion inducing element is translated out of the way so that the motion inducing element does not hinder the abduction motion. When the humeral liner is abducted and rotated, the motion inducing element does not translate because a force is applied off axis from the slot and as such the motion inducing element remains fixed and causes the type of motion to be converted in the same manner as the nonmodular feature.

FIGS. 9A-9C show an embodiment of a glenoid component 900 of the present invention. Glenoid component 900 comprises a glenosphere 910 and a glenoid plate 920. In an embodiment, the glenosphere 910 and the glenoid plate 920 may be formed as in integral unit. In an embodiment, the glenosphere 910 and the glenoid plate 920 are two distinct components affixed together in a modular configuration. In an embodiment, the glenosphere 910 is assembled to the glenoid plate 920 using an assembly bolt passing through hole 912. In an embodiment, the glenosphere 910 does not include hole 912. Glenosphere 910, which may be constructed, for example, from cobalt chrome, includes a convex articulating surface 915 having a motion inducing spherical element 940, the motion inducing spherical element 940 sufficiently designed to travel or translate in a slot 950 having a first end 950a and a second end 950b. The slot 950 is designed so that the motion inducing spherical element 940 can slide within the full length of the slot 950, from the first end 950a to the second end 950b and back to the first end 950a. In an embodiment, the motion inducing spherical element 940 has a diameter ranging from about 0.08 inches to about 0.50 inches, from about 0.10 inches to about 0.40 inches, from about 0.20 inches to about 0.30 inches. In an embodiment, the motion inducing spherical element 940 has a diameter of about 0.25 inches. In an embodiment, the motion inducing spherical element 940 has a height ranging from about 0.035 inches to about 0.250 inches, from about 0.040 inches to about 0.155 inches, from about 0.045 inches to about 0.150 inches, from about 0.050 inches to about 0.145 inches, from about 0.055 inches to about 0.140 inches, from about 0.060 inches to about 0.135 inches, from about 0.065 inches to about 0.130 inches, from about 0.070 inches to about 0.125 inches, from about 0.075 inches to about 0.120 inches, from about 0.080 inches to about 0.115 inches. In an embodiment, the motion inducing spherical element 940 has a height of about 0.14 inches. In an embodiment, the glenoid plate 920, which may be constructed, for example, from titanium, includes a bone "through-growth" cage stem 930 which enables bone graft to be injected (e.g., via syringe) through the front of the plate and/or placed through the hole in the bottom surface of the cage stem 930. In an embodiment, the bone "through-growth" cage stem 930 is superiorly shifted (for example, by about 4 mm) from the central point of the vertical dimension on the glenoid plate 920—enabling a surgeon to maintain the traditional surgical technique with the reverse as would be performed for total shoulder arthroplasty (i.e., drilling a hole in the center of the glenoid where the defect would occur; thereby conserving bone). In an embodiment, the glenoid plate 920 has the following dimensions/features: 29 mm diameter, 5 mm taper, 20 mm length bone "through-growth" cage stem 930 with screw holes having a spherical base allowing compression screws to be angled at about 15°, each hole having a threaded portion for attachment of a locking cap screw.

In an embodiment, the glenosphere 910 and the glenoid plate 920 are components of a reverse shoulder assembly of the present invention which may be implanted at a shoulder joint in a patient. During use, the motion inducing spherical element 940 is sufficiently designed and positioned on the glenosphere 910 so as to alter the direction of the induced motion at varying humeral positions. By selecting the positioning of the motion inducing spherical element 940 on the articulating surface 915, different types of motion can be induced. In an embodiment, the motion inducing spherical element 940 and the slot 950 are sufficiently designed so that when the patient raises his/her arm to a certain degree of shoulder abduction, the abduction motion is altered into a forward flexion motion.

In an embodiment, the glenoid component 900 and the humeral component 300, 700 or 800 form a reverse shoulder assembly of the present invention used for treating rotator cuff tear arthroplasty. In an embodiment, the slot 950 is sufficiently designed to limit the effect of unintended contact between the motion inducing humeral liner surface 340, 750 or 850 and the motion inducing spherical element 940. To limit the possibility of lever out dislocation that could result from inadvertent contact between the motion inducing humeral liner surface 340, 750 or 850 and the motion inducing spherical element 940, the motion inducing spherical element 940 can be made to be modular and inserted into the slot 950 in the glenosphere 910 so that when the patient raises his/her arm to a certain degree of shoulder abduction, the motion inducing humeral liner surface 340, 750 or 850 contacts the motion inducing spherical element 940 and translates the motion inducing spherical element 940 until the slot 950 ends, at which point the abduction motion would be converted to a forward flexion motion. As illustrated in FIGS. 9A-9C, the slot 950 runs from inferior to superior so as to not impede the patient from achieving full abduction. In an embodiment, the slot 950 has a width ranging from about 0.09 inches to about 0.51 inches, from about 0.08 inches to about 0.50 inches, from about 0.10 inches to about 0.40 inches, from about 0.20 inches to about 0.30 inches. In an embodiment, the width of the slot 950 is about 0.26 inches. In an embodiment, the slot 950 has a length that can be determined based upon the amount of abduction that is desired to be preserved relative to the placement of the slot 950 (i.e., where the slot 950 starts). In an embodiment, the slot 950 has a length ranging from about 0.10 inches to about 1.00 inches, from about 0.15 inches to about 0.95 inches, from about 0.20 inches to about 0.90 inches, from about 0.25 inches to about 0.90 inches, from about 0.30 inches to about 0.85 inches, from about 0.35 inches to about 0.80 inches, from about 0.40 inches to about 0.75 inches, from about 0.45 inches to about 0.70 inches, from about 0.50 inches to about 0.65 inches, from about 0.55 inches to about 0.60 inches. In an embodiment, the slot 950 has a length of about 0.55 inches. Although FIGS. 9A-9C show an embodiment of a slot 950 having a specific size, specific shape and specific orientation (inferior to superior), it should be understood that other sizes, shapes and orientations for slot 950 are possible as not all embodiments are limited to what is illustrated in FIGS. 9A-9C.

In an embodiment, the position and/or geometry of the motion inducing element 140, 240 or 940 can be modified to alter the direction of the induced motion at varying humeral positions. In an embodiment, the motion inducing element is cylindrical in shape (see, for example, 140 of FIGS. 1A-1C). In an embodiment, the motion inducing element is spherical in shape (see, for example, 240 of FIGS. 2A-2C and 940 of FIGS. 9A-9C). In an embodiment, the motion inducing spherical element 240 or 940 allows for a greater degree of freedom during induced motion. In an embodiment, a motion inducing element has a more complex (e.g., asymmetric) geometry which could change the direction and/or magnitude of the induced motion at varying humeral positions. In an embodiment, the motion inducing element of the present invention may be constructed, for example, from a biocompatible plastic or a biocompatible metal. In an embodiment, the motion inducing element 140, 240 or 940 can be constructed from the same material as the glenosphere 110, 210 or 910, for example, cobalt chrome. In an embodiment, the motion inducing element 140, 240 or 940 can be constructed from a different material then the glenosphere 110, 210 or 910, for example, UHMWPE. In an embodiment, the material (s) of the motion inducing element 140, 240 or 940 may be modified. In an embodiment, the surface finish of the motion inducing element 140, 240 or 940 may be modified. In an embodiment, the geometry of the motion inducing element 140, 240 or 940 and/or the motion inducing humeral liner surface 340, 750 or 850 may be modified to improve the performance of a reverse shoulder assembly of the present invention (e.g., limiting wear/preventing fracture) and/or at the same time assisting a patient to maintain the arm at new positions (e.g., by balancing the internal rotation force and the nonexistent external rotation force via friction and/or mechanical interlock).

Although the embodiments illustrated in FIGS. 1A-9C show the glenosphere 110, 210 and 910 comprising the motion inducing element 140, 240 and 940, and the humeral liner 310, 710 and 810 comprising the motion inducing humeral liner surface 340, 750 and 850, it should be understood that various other designs are within the scope and spirit of the present invention. In some embodiments, a glenosphere of the present invention comprises at least one motion inducing guiding surface, and a humeral liner of the present invention comprises at least one motion inducing element.

FIGS. 10A-10C show an embodiment of a glenoid component 1000 of the present invention. Glenoid component 1000 comprises a glenosphere 1010 and a glenoid plate 1020. In an embodiment, the glenosphere 1010 and the glenoid plate 1020 are two distinct components affixed together in a modular configuration. In an embodiment, the glenosphere 1010 is assembled to the glenoid plate 1020 using an assembly bolt passing through hole 1012. In an embodiment, the glenosphere 1010 does not include hole 1012. In an embodiment, the glenosphere 1010 and the glenoid plate 1020 may be formed as in integral unit. Glenosphere 1010, which may be constructed, for example, from cobalt chrome, includes a convex articulating surface 1015, a recess area 1040, and a motion inducing guiding surface 1050. In an embodiment, the recess area 1040 has a depth that is variable and is from about 0.040 inches to about 0.255 inches, from about 0.035 inches to about 0.250 inches, from about 0.040 inches to about 0.155 inches, from about 0.045 inches to about 0.150 inches, from about 0.050 inches to about 0.145 inches, from about 0.055 inches to about 0.140 inches, from about 0.060 inches to about 0.135 inches, from about 0.065 inches to about 0.130 inches, from about 0.070 inches to about 0.125 inches, from about 0.075 inches to about 0.120 inches, from about 0.080 inches to about 0.115 inches. In an embodiment, the recess area 1040 has a depth of about 0.19 inches. In an embodiment, the depth of the recess area 1040 is measured from the articulating surface 1015. In an embodiment, the glenoid plate 1020, which may be constructed, for example, from titanium, includes a bone "through-growth" cage stem 1030 which enables bone graft to be injected (e.g., via syringe) through the front of the plate and/or placed through the hole in the bottom surface of the cage stem 1030. In an embodiment, the bone "through-growth" cage stem 1030 is superiorly shifted (for example, by about 4 mm) from the central point of the vertical dimension on the glenoid plate 1020—enabling a surgeon to maintain the traditional surgical technique with the reverse as would be performed for total shoulder arthroplasty (i.e., drilling a hole in the center of the glenoid where the defect would occur; thereby conserving bone). In an embodiment, the glenoid plate 1020 has the following dimensions/ features: 29 mm diameter, 5 mm taper, 20 mm length bone "through-growth" cage stem 1030 with screw holes having a spherical base allowing compression screws to be angled at about 15 degrees, each hole having a threaded portion for attachment of a locking cap screw.

FIGS. 11A-11D show an embodiment of a humeral component 1100 of the present invention. Humeral component 1100 comprises humeral stem 1105, which may be used in either pressfit or cemented applications and may be constructed, for example from titanium; a humeral liner 1110, which may be constructed, for example, from UHMWPE; and a humeral adapter plate 1120, which connects the humeral liner 1110 to the humeral stem 1105 and may be constructed, for example, from titanium. Humeral liner 1110 comprises a concave articulating surface 1115 that is sufficiently designed to engage with the articulating surface 1015 of the convex glenosphere 1010. The articulating surface 1115 comprises a motion inducing spherical element 1140. In an embodiment, the motion inducing spherical element 1040 has a diameter ranging from about 0.08 inches to about 0.50 inches, from about 0.10 inches to about 0.40 inches, from about 0.20 inches to about 0.30 inches. In an embodiment, the motion inducing spherical element 1040 has a diameter of about 0.25 inches. In an embodiment, the motion inducing spherical element 1040 has a height ranging from about 0.035 inches to about 0.250 inches, from about 0.040 inches to about 0.155 inches, from about 0.045 inches to about 0.150 inches, from about 0.050 inches to about 0.145 inches, from about 0.055 inches to about 0.140 inches, from about 0.060 inches to about 0.135 inches, from about 0.065 inches to about 0.130 inches, from about 0.070 inches to about 0.125 inches, from about 0.075 inches to about 0.120 inches, from about 0.080 inches to about 0.115 inches. In an embodiment, the motion inducing spherical element 1040 has a height of about 0.14 inches.

In an embodiment, the humeral component 1100 and the glenoid component 1000 form a reverse shoulder assembly of the present invention. The reverse shoulder assembly may be used to treat patients having a condition including, but not limited to, rotator cuff tear arthroplasty, instability with anterosuperior escape, pseudoparalysis, and failures of surgery for arthritis and facture management In an embodiment, the reverse shoulder assembly may be used for patients with rotator cuff tear arthropathy (end stage cuff tear arthropathy) a medical condition in which the rotator cuff muscles (the muscles around the shoulder joint) have degenerated, or weakened to a point where they can no longer hold the shoulder joint intact or allow it to function normally in conjunction with arthritis. In an embodiment, the reverse shoulder assembly may be used for patients needing revision surgery, for failed shoulder replacement and shoulder fractures. In an embodiment, the reverse shoulder assembly may be used for patients who do not have a rotator cuff (pseudo-paralytic shoulder).

During use, the articulating surface 1015 of the glenosphere 1010 engages the articulating surface 1115 of the humeral liner 1110. The motion inducing spherical element 1140 is sufficiently designed and positioned on the articulating surface 1115 of the humeral liner 1110 so as to alter the direction of induced motion at varying humeral positions. By selecting the positioning of the motion inducing spherical element 1140 on the articulating surface 1115, different types of motion can be induced. In an embodiment, the motion inducing spherical element 1140 is positioned on the articulating surface 1115 so that when the patient raises his/her arm out to the side (i.e., shoulder abduction or lateral arm raise), the abduction motion is altered into an external rotation motion. In an embodiment, the motion inducing spherical element 1140 is positioned on the articulating surface 1115 so that when the patient raises his/her arm out to the side (i.e., shoulder abduction or lateral arm raise), the abduction motion is altered into a forward flexion motion. In an embodiment, the motion inducing spherical element 1140 is positioned on the articulating surface 1115 so that when the patient raises his/her arm out to the side (i.e., shoulder abduction or lateral arm raise), the abduction motion is altered into an external rotation and a forward flexion motion.

In an embodiment, the amount of material recessed from the articulating surface 1015 is variable and is dependent upon the specific angle of abduction in which it is desired that the motion inducing features become engaged. In an embodiment, the depth of the recess area 1040 is determined after selecting the height of the motion inducing element 1140. The depth of the recess area 1040 should be larger than the height of the motion inducing element 1140 so that when the motion inducing element 1140 interacts with the motion inducing humeral liner surface 1050, the articulating surface 1115 does not contact the recess area 1040.

In another example, a reverse shoulder assembly may be provided in a left-side version and/or a right-side version (e.g., a forward flexion reverse shoulder assembly having a flexion inducing glenosphere and/or humeral liner configured for use on the left side of the body and/or a forward flexion reverse shoulder assembly having a flexion inducing glenosphere and/or humeral liner configured for use on the right side of the body).

In an embodiment, a reverse shoulder assembly of the present invention includes a glenoid component and a humeral component disclosed herein. In an embodiment, a reverse shoulder assembly of the present invention is used for the treatment of rotator cuff tear. In an embodiment, a reverse shoulder assembly of the present invention is used for the treatment of shoulder joint pain. In an embodiment, a reverse shoulder assembly of the present invention is used for the treatment of rotator cuff tear arthropathy (shoulder arthritis with a massive rotator cuff tear). In an embodiment, a reverse shoulder assembly of the present invention is used for the treatment of pseudoparalysis of the shoulder. In an embodiment, a reverse shoulder assembly of the present invention is used for the treatment of rheumatoid arthritis of the shoulder. In an embodiment, a reverse shoulder assembly of the present invention is used for the treatment of bone tumors around the shoulder joint. In an embodiment, a reverse shoulder assembly of the present invention is used for the treatment of advanced osteonecrosis. In an embodiment, a reverse shoulder assembly of the present invention is used for patients needing revision surgery, for failed shoulder replacement and shoulder fractures. In an embodiment, a reverse shoulder assembly of the present invention is used for patients who do not have a rotator cuff (pseudo-paralytic shoulder).

In another embodiment, a method of reconstructing a diseased shoulder is provided, comprising: providing a glenoid component comprising an articulating surface having a motion inducing element and a humeral liner comprising a motion inducing humeral liner surface, wherein the motion inducing element interacts with the motion inducing humeral liner surface to alter the abduction motion of a humerus relative to a scapula into a forward flexion motion of the humerus relative to the scapula.

It has been shown in the literature that only two-thirds of shoulder abduction occurs in the glenohumeral joint, the remaining third taking place via scapular rotation. In an embodiment, a patient receiving a reverse shoulder prosthesis of the present invention has muscle deficiencies which prevent them from achieving internal or external rotation or more complex motions which require either internal or external rotation in combination with another type of motion. In such embodiments, the motion inducing element and the motion inducing humeral liner surface of the prosthesis are sufficiently designed to interact with one another and help drive the kinematic motion of the shoulder joint. In such embodiments, the motion inducing element and the motion inducing humeral liner surface achieve essentially the same active result as the typical clinical solution (e.g., muscle transfers) for patients with external rotation deficit.

In another embodiment, a method of reconstructing a diseased shoulder is provided, comprising: providing a glenoid component comprising a motion inducing guiding surface and a humeral liner comprising an articulating surface having a motion inducing element which interact to alter the abduction motion of a humerus relative to a scapula into a forward flexion motion of the humerus relative to the scapula.

While a number of embodiments of the present invention have been described, it is understood that these embodiments are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone ingrowth or prohibit surface bone ingrowth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel, cobalt chrome); (f) any combination thereof. Further still, any metal construct may be a machined metal construct. Further still, any number of protrusions (e.g., such as for initial fixation by forming a bond with cement and/or such as for supplemental fixation by forming a bond with cement) may be utilized with a given prosthesis. Further still, any number of female features that increase the cement mantle may be utilized with a given prosthesis. Further still, any number of male features that could dig into the bone so that initial/supplemental fixation can be improved may be utilized with a given prosthesis. Further still, any number of bone screws (e.g., such as for initial fixation and/or such as for supplemental fixation) may be utilized with a given prosthesis. Further still, any element(s) or component(s) described herein may be combined with any other element(s) or component(s) described herein. Further still, any element(s) or component(s) described herein may be used on or in conjunction with any other element(s) or component(s) described herein. Further still, the fixation stem may be configured to be hollow, have hole(s) in the sidewall and/or have an open end to aid in receiving bone growth inducing material and/or to aid in bone ingrowth for fixation. Further still, any steps described herein may be carried out in any desired order (and any additional steps may be added as desired and/or any steps may be deleted as desired).

What is claimed is:
1. A reverse shoulder assembly comprising:
a glenoid component comprising a glenosphere and a glenoid attachment means; and
a humeral component,
wherein the humeral component comprises a humeral liner, a humeral attachment means, and a humeral adapter plate which connects the humeral liner to the humeral attachment means, wherein the humeral liner comprises a concave articulating surface, wherein the concave articulating surface comprises a motion inducing element formed thereon, said motion inducing element is in the shape of a cam, wherein the glenoid component comprises a convex articulating surface designed to articulate with the concave articulating surface of the humeral liner, the convex articulating surface comprising a motion inducing guiding surface, wherein the motion inducing element and the motion inducing guiding surface are sufficiently designed so that, when the glenoid component is implanted in a glenoid, and when the humeral component is implanted in a humerus, an interaction between the motion inducing element and the motion inducing guiding surface alters the abduction motion of the humerus relative to a scapula into a forward flexion motion of the humerus relative to the scapula, wherein the interaction between the motion inducing element and the motion inducing guiding surface further alters the abduction motion of the humerus relative to the scapula into an external rotation motion of the humerus relative to the scapula, wherein the motion inducing element has a geometry capable of altering the direction of the induced motion at varying humeral positions.

2. The assembly of claim 1 wherein the motion inducing element has a spherical geometry.

3. The assembly of claim 1 wherein the motion inducing element is sufficiently positioned on the articulating surface of the humeral liner to alter the direction of the induced motion at varying humeral positions.

4. The assembly of claim 1 wherein at approximately 60 degree abduction motion of the humerus relative to the scapula, the motion inducing element engages the motion inducing guiding surface.

5. The assembly of claim 1 wherein at approximately 70 degree abduction motion of the humerus relative to the scapula, the motion inducing element moves along the motion inducing guiding surface and induces approximately 10 degrees of forward flexion of the humerus relative to the scapula.

6. The assembly of claim 1 wherein at approximately 90 degree abduction motion of the humerus relative to the scapula, the motion inducing element moves along the motion inducing guiding surface and induces approximately 20 degrees of forward flexion of the humerus relative to the scapula.

7. The assembly of claim 1 wherein between about 30 degrees and about 90 degrees abduction motion of the humerus relative to the scapula, the motion inducing element initially engages the motion inducing guiding surface.

8. The assembly of claim 1 wherein the glenoid component further comprises a glenoid plate.

* * * * *